United States Patent
Schwab et al.

(10) Patent No.: US 10,201,706 B2
(45) Date of Patent: Feb. 12, 2019

(54) SYSTEMS AND METHODS OF IMPROVING AN INFLAMMATORY DISORDER

(71) Applicant: Ohio State Innovation Foundation, Columbus, OH (US)

(72) Inventors: Jan Schwab, Columbus, OH (US); Phillip Popovich, Columbus, OH (US); Ali R. Rezai, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/382,950

(22) Filed: Dec. 19, 2016

(65) Prior Publication Data

US 2017/0120046 A1 May 4, 2017

Related U.S. Application Data

(63) Continuation-in-part of application No. 15/155,466, filed on May 16, 2016.

(60) Provisional application No. 62/162,261, filed on May 15, 2015, provisional application No. 62/180,760, filed on Jun. 17, 2015.

(51) Int. Cl.
| | |
|---|---|
| *A61N 1/36* | (2006.01) |
| *A61M 5/172* | (2006.01) |
| *A61M 5/142* | (2006.01) |
| *A61N 7/00* | (2006.01) |
| *A61N 5/06* | (2006.01) |

(52) U.S. Cl.
CPC ....... *A61N 1/3606* (2013.01); *A61M 5/14276* (2013.01); *A61M 5/1723* (2013.01); *A61N 1/36014* (2013.01); *A61N 2005/0659* (2013.01); *A61N 2007/0026* (2013.01)

(58) Field of Classification Search
CPC ...... A61N 1/205; A61N 1/36007; A61N 1/40; A61N 1/3606; A61N 1/3601; A61N 2/006; A61N 5/0622; A61N 5/02; A61N 7/00; A61N 2007/0026; A61N 2005/0659
See application file for complete search history.

(56) References Cited

U.S. PATENT DOCUMENTS

| | | |
|---|---|---|
| 7,418,292 B2 | 8/2008 | Shafer |
| 8,195,287 B2 | 6/2012 | Dacey, Jr. et al. |
| 2003/0018368 A1 | 1/2003 | Ansarinia |
| 2004/0215265 A1 | 10/2004 | Keizer |

(Continued)

FOREIGN PATENT DOCUMENTS

| | | |
|---|---|---|
| WO | 2016072875 A1 | 5/2016 |
| WO | 2016134199 A1 | 8/2016 |
| WO | 2016138176 A1 | 9/2016 |

OTHER PUBLICATIONS

PCT International Search Report and Written Opinion for PCT/US2016/032690, dated Sep. 12, 2016, pp. 1-13.

(Continued)

*Primary Examiner* — Rex R Holmes
(74) *Attorney, Agent, or Firm* — Meunier Carlin & Curfman LLC (57) ABSTRACT

Methods for improving an inflammatory disorder in a subject are provided. Methods include positioning a therapy delivery device on a neural target site that contributes to immune activity of the subject. The therapy delivery device is activated to deliver a therapy signal to the neural target site to improve the subject's inflammatory disorder.

19 Claims, 6 Drawing Sheets

(56) References Cited

U.S. PATENT DOCUMENTS

| | | | |
|---|---|---|---|
| 2005/0075701 A1* | 4/2005 | Shafer | A61N 1/36017 607/72 |
| 2006/0047325 A1 | 3/2006 | Thimineur et al. | |
| 2006/0167498 A1 | 7/2006 | DiLorenzo | |
| 2006/0287678 A1 | 12/2006 | Shafer | |
| 2007/0208382 A1* | 9/2007 | Yun | A61N 1/36007 607/2 |
| 2009/0157149 A1 | 6/2009 | Wahlgren et al. | |
| 2010/0241183 A1 | 9/2010 | DiLorenzo | |
| 2010/0249859 A1 | 9/2010 | DiLorenzo | |
| 2011/0184486 A1 | 7/2011 | De Ridder | |
| 2011/0238128 A1 | 9/2011 | Dobak, III | |
| 2014/0277326 A1 | 9/2014 | Rhodes | |
| 2014/0330068 A1* | 11/2014 | Partsch | A61N 2/02 600/13 |
| 2014/0350041 A1 | 11/2014 | Yun et al. | |
| 2015/0111918 A1 | 4/2015 | Sobotka et al. | |
| 2016/0045726 A1 | 2/2016 | Redington | |
| 2016/0331962 A1 | 11/2016 | Schwab et al. | |
| 2017/0100588 A1 | 4/2017 | Schwab et al. | |
| 2017/0100589 A1 | 4/2017 | Schwab et al. | |
| 2017/0100604 A1 | 4/2017 | Schwab et al. | |

OTHER PUBLICATIONS

Geerlings, Suzanne E., and Andy IM Hoepelman. "Immune dysfunction in patients with diabetes mellitus (DM)." Pathogens and Disease 26.3-4 (1999): 259-265.

Haque, Raqeeb, and Christopher J. Winfree. "Spinal nerve root stimulation." Neurosurgical focus 21.6 (2006): 1-7.

International Search Report and Written Opinion of the International Searching Authority, issued in International Application No. PCT/US2017/067213 dated Mar. 7, 2018, 8 pages.

International Search Report and Written Opinion of the International Searching Authority, issued in International Application No. PCT/US2017/067217 dated Jan. 19, 2018, 10 pages.

International Search Report and Written Opinion of the International Searching Authority, issued in International Application No. PCT/US2017/067218 dated Mar. 8, 2018, 7 pages.

International Search Report and Written Opinion of the International Searching Authority, issued in International Application No. PCT/US2017/067221 dated Mar. 1, 2018, 10 pages.

International Search Report and Written Opinion of the International Searching Authority, issued in International Application No. PCT/US2017/067223 dated Mar. 8, 2018, 7 pages.

Val-Laillet, David, et al. "Neuroimaging and neuromodulation approaches to study eating behavior and prevent and treat eating disorders and obesity." NeuroImage: Clinical 8 (2015): 1-31.

\* cited by examiner

SYSTEMS AND METHODS OF IMPROVING AN INFLAMMATORY DISORDER

RELATED APPLICATIONS

This application is a continuation-in-part of U.S. application Ser. No. 15/155,466, filed on May 16, 2016, which claims priority to U.S. Provisional Patent Application Ser. No. 62/162,261, filed May 15, 2015, and U.S. Provisional Application No. 62/180,760, filed on Jun. 17, 2015. The entirety of all the aforementioned applications is hereby incorporated by reference for all purposes.

TECHNICAL FIELD

The present disclosure generally relates to improving a patient's immune and inflammation response by neuromodulation and other forms of therapy.

The central nervous system (CNS) controls the immune system by several pathways, including being hardwired to the autonomic nervous system (ANS). Sensors within the central and peripheral autonomic system (PNS) relay information about the status of the immune system. Disruption of coordinated CNS-immune system interaction after injury or disease can result in an abrupt and drastic increase or decrease in immune function.

A need exists for methods to balance tune, optimize, normalize, enhance, increase or decrease sympathetic tone and function in patients suffering from immune-related diseases or conditions.

SUMMARY

In an embodiment, a method of improving an inflammatory disorder in a subject suffering therefrom is provided. The method involves positioning a therapy delivery device in communication with a neural target site that contributes and modulates the to immune activity of the subject and activating the therapy delivery device to deliver a therapy signal to the neural target site to improving the subject's inflammatory disorder.

In another embodiment, a method for improving an inflammatory disorder is provided that includes determining the level of a physiological parameter that is indicative of immune activity of a subject and predicting dysfunction of the subject's immune and inflammation system by comparing the determined level of the physiological parameter with a control value. The method further includes placing a therapy delivery device into electrical communication with a neural target site that contributes to immune activity if the subject suffers from immune system dysfunction. The method further includes activating the therapy delivery device to deliver a therapy signal to the neural target site to improve the subject's inflammatory disorder.

BRIEF DESCRIPTION OF THE DRAWINGS

FIG. 2 is a schematic illustration of the levels of integration of the sympathetic (autonomic) nervous system and their implications after CNS injury according to an embodiment of the present disclosure: (A) Schematized supraspinal centers (brainstem and brain) versus spinal cord mapping to neuroendocrine and immunological effector organs; and (B) Traumatic brain injury (TBI), stroke, subarachnoid hemorrhage and iatrogenic injury after brain tumor removal are prevalent causes for damage to supraspinal centers. Spinal cord injury damages spinal interneurons and autonomic pre-ganglionic neurons. As a consequence of injury at all depicted anatomical locations—either of traumatic or non-traumatic origin—disinhibited sympathetic nerve activity (SNA) will enter neuroendocrine and immunological effector organs and result in immune suppression;

DETAILED DESCRIPTION

The present disclosure is generally directed to improving a patient's immune function. Improving a patient's immune function includes normalizing, modulating, optimizing, tuning restoring, regulating, increasing immune activity and function, or decreasing immune activity and function so that the patient's immune system is modulated to improve hyperactive, hypoactive, or otherwise abnormal immune and inflammatory systems to improve symptoms of the subject that are caused by the abnormal immune system.

As used herein with respect to a described element, the terms "a," "an," and "the" include at least one or more of the described element unless otherwise indicated. Further, the term "or" and "and" refer to "and/or" unless otherwise indicated. It will be understood that when an element is referred to as being "over," "on," "attached" to, "connected" to, "coupled" with, "contacting," "in communication with," etc., another element, it can be directly over, directly on, attached to, connected to, coupled with, contacting, or in communication with the other element or intervening elements may also be present. In contrast, when an element is referred to as being "directly over," "directly on," "directly attached" to, "directly connected" to, "directly coupled" with, "directly contacting," or in "direct communication" with another element, there are no intervening elements present. An element that is disposed "adjacent" another element may have portions that overlap or underlie the adjacent element.

In addition, when exemplary target sites are disclosed, combination of such target sites are also included as part of the disclosed target site.

As used herein, the term "subject" can be used interchangeably with the term "patient" and refers to any warm-blooded organism including human beings and domesticated animals. Domesticated animals include livestock such as, for example, pigs, goats, sheep, chicken, horses, and cattle; and domesticated pets such as dogs and cats.

As used herein, the term "electrical communication" refers to the ability of an electric field generated by an electrode to be transferred to neural tissue.

As used herein, the term "abnormal" immune activity is decreased, increased, imbalanced, or impaired immune activity as compared to the immune activity of a healthy subject. A healthy subject is a subject who has not previously been diagnosed as having any signs or symptoms indicating the presence of an immune system dysfunction, a history of immune system dysfunction, or evidence of immune system dysfunction. A healthy subject is also a subject who, if examined by a medical professional, would be characterized as free of immune system dysfunction.

As used herein, the term "neural target site" refers to a target site of the body that receives input from or delivers input to nervous system tissue.

Figure 1:
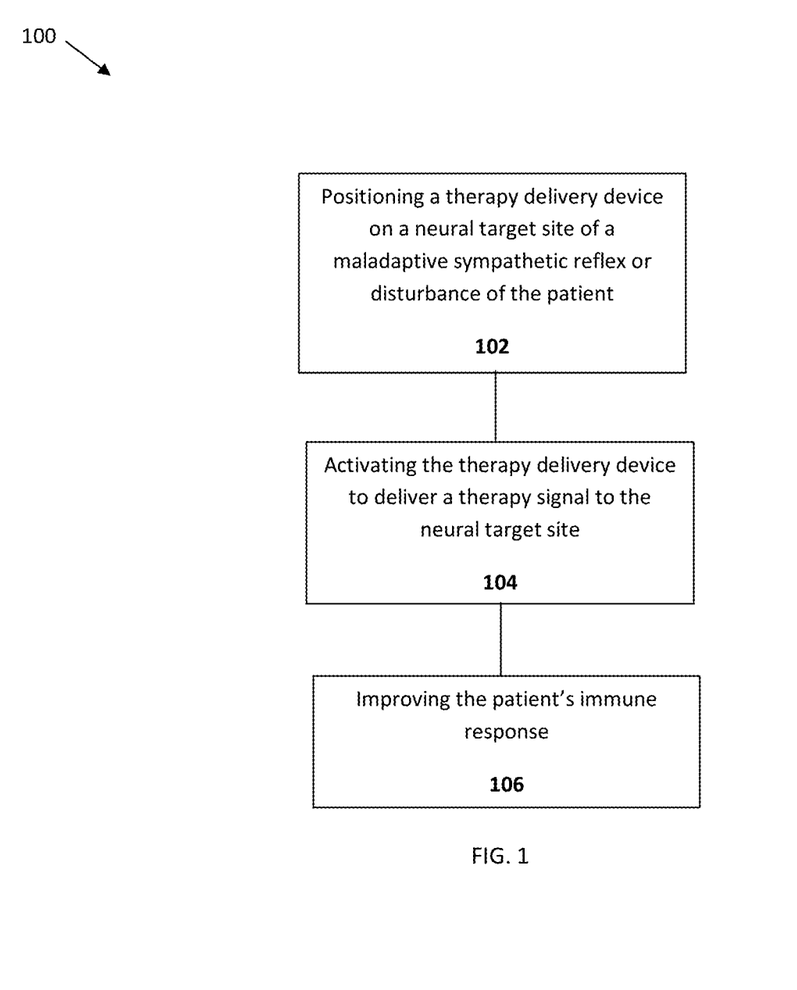
FIG. 1 is a process flow diagram illustrating a method for modulating immune function in a patient according to an embodiment of the present disclosure.

Referring to FIG. 1, in general, a method 100 of improving an immune response in a patient suffering from a condition resulting or caused by an abnormal or deficient immune system comprises positioning a therapy delivery device in communication with a neural target site of a maladaptive sympathetic reflex or disturbance of the patient 102. The therapy delivery device is activated to deliver a therapy signal to the neural target site 104 to improve the patient's immune response 106.

The neural target site can be a PNS or a CNS structure anatomically relevant to maladaptive sympathetic reflexes or disturbances. Preferably, the neural target site innervates an endocrinological or lymphatic tissue or organ involved in the immune response and inflammatory response and state of the patient. In certain embodiments, the neural target site is a neural target site of the ANS. For example, the neural target site can be a celiac ganglion, a superior mesenteric ganglion, an aorticorenal ganglion, a renal plexus, a inferior mesenteric ganglion, a superior hypogastric ganglion, a lumbar plexus, a celiac plexus, a splenic nerve, a sympathetic trunk, a splanchnic nerve, an intrinisic nervous system of an organ, and their input and output nervous system structures. In other embodiments, the neural target site can be the spinal cord (including the thoracic, cervical, and lumbar segments), a dorsal root ganglion, a pre-ganglionic fiber, a post-ganglionic fiber, or an adrenal nerve. The neural target site can be other central regions such as within the forebrain, including the hypothalamus; the insular cortex; the nucleus coeruleus; or the prefrontal cortex and brainstem including the midbrain-pons-medulla circuitry that controls output from the spinal cord to immune organs. Such central structures or neural regions directly "map" to spinal cord interneurons or sympathetic preganglionic neurons and subsequently to peripheral neural target sites such as ganglia controlling immune organs. In other embodiments, the neural target site is part of the enteric nervous system, such as a nerve, ganglion or plexus of the enteric nervous system. In certain embodiments, the neural target site is pre-ganglionic fibers in the spinal cord efferent fibers and the intermediolateral column; epidural spinal cord; ventral (VRG) and dorsal roots (DRG); DRG afferent fibers, the doral horn; white rami; gray rami; sympathetic ganglia and the sympathetic chain, thoracic splanchnic nerves; para-aortic ganglia, such as the celiac ganglion; sympathetic plexus; or post ganglionic fibers.

Figure 1A:
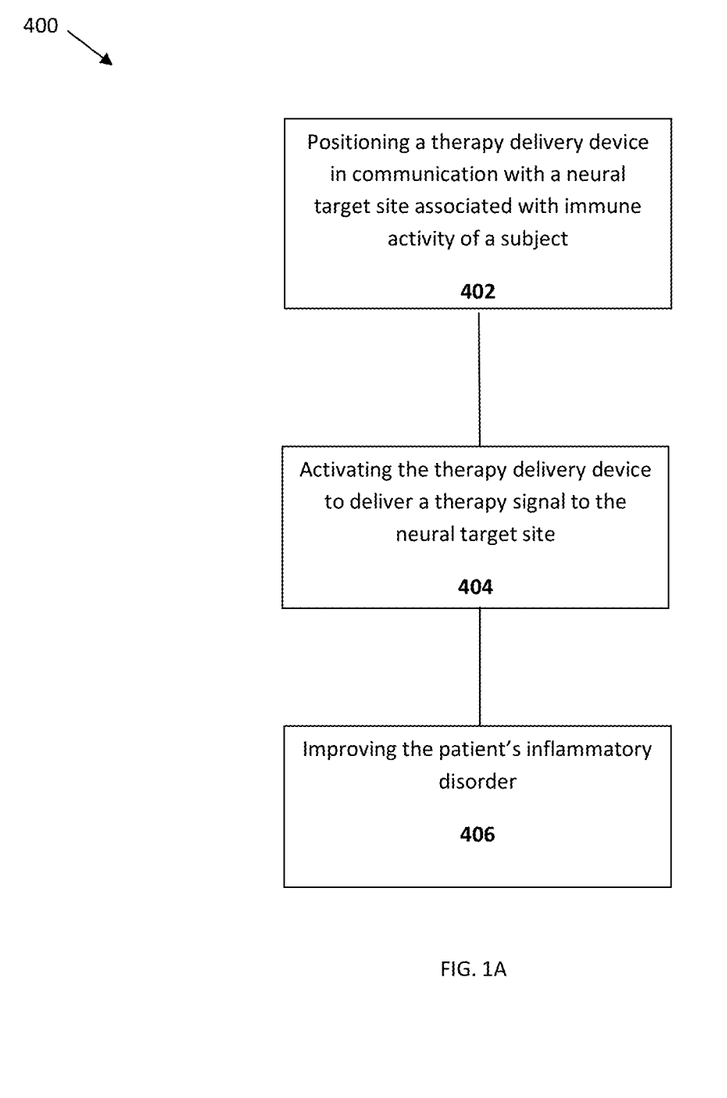
FIG. 1A is a process flow diagram illustrating a method for improving an inflammatory disorder in a subject according to an embodiment of the present disclosure.

Referring to FIG. 1A, in certain embodiments, a method 400 includes improving an inflammatory disorder in a subject suffering therefrom by positioning a therapy delivery device in communication with a neural target site that contributes to immune activity of a subject 402. The method further includes activating the therapy delivery device to deliver a therapy signal to the neural target site 404 and improving the subject's inflammatory disorder 406. By improving the subject's inflammatory disorder, the symptoms caused by the inflammatory disorder are alleviated. Symptoms vary based on the type and location of the inflammation.

An inflammatory disorder is a disorder in which a break in homeostasis or a failure to restore homeostasis causes excessive recruitment and activation of innate (and occasionally adaptive) immune cells often without physiological resolution (e.g. chronic inflammation). Symptoms of an inflammatory disorder include, for example, chronic pain, redness, swelling, stiffness, or damage to normal cells. Inflammatory disorders include disorders caused by a defective, excessive or non-resolving acute inflammatory reaction such as, for example, serous inflammation, fibrinous inflammation, suppurative or purulent inflammation, or leukocyte-induced injury. Inflammatory disorders also include disorders caused by defective or excessive chronic inflammation such as, for example, ulcers, granulomatous inflammation or leukocyte-induced injury. Non-limiting examples of inflammatory disorders are atherosclerosis; inflammatory bowel diseases, such as Crohn's disease and ulcerative colitis; non-allergic asthma; acute respiratory distress syndrome (ARDS); acute lung injury (ALI); chronic respiratory distress syndrome (CRDS); dermatitis; gout; eczema, gastritis; hepatitis; prostatitis; sinusitis; splenitis; nephritis; inflammation of body organs including joint inflammation including joints in the knees, limbs or hands; and neurogenic lung edema.

In certain embodiments, a method of improving an inflammatory disorder includes improving tolerability of long-lasting immune modulatory therapy. Such a method can be used when orthodox immune modulatory treatment (e.g. steroids) cannot be provided because of limiting side effects of such treatment. Such side effects include, for example, osteoporosis and psychosis. As such, an exemplary method involves a corticosteroid sparing approach, which allows for better treatment tolerability. This can be advantageous in chronically ill patients when long lasting therapy regimens are required. In such embodiments, the patient population is patients that cannot tolerate corticosteroids or other pharmaceutical (e.g. drug) or biological agents to improve their inflammatory disorder. To not "tolerate" such agents, is meant that the side effects associated with the administration of such agents is greater than the therapeutic benefit gained by such agents. In certain embodiments, a method of improving an inflammatory disorder comprises positioning a therapy delivery device in communication with a neural target site that contributes to immune activity of a subject. The method further includes activating the therapy delivery device to deliver a therapy signal to the neural target site and improving the subject's inflammatory disorder. The subject's inflammatory disorder is improved without the administration of corticosteroids or other pharmaceutical agents that are indicated for treating or otherwise improving inflammatory disorders.

As stated above, a method of improving an inflammatory disorder includes positioning a therapy delivery device in communication with a neural target site that contributes to immune activity. Such neural target sites can be part of the brain, spinal cord, PNS or enteric nervous system. For example, with respect to the brain, the neural target site can be the hypothalamus, insular cortex, nucleus coeruleus, or the pre-frontal cortex. The neural target site can also be the brainstem including the pons (which includes pontine noradrenergic cell groups and the pontine reticular formation) or the medulla. With respect to the spinal cord, the neural target site can be a cervical, thoracic or lumbar segment, such as a C1-S5 segment. In certain embodiments, the neural target site is a thoracic spinal segment, which is the origin of pre-ganglionic sympathetic neurons. With respect to the PNS, the neural target site can be a site of the ANS, which includes the sympathetic nervous system (SNS) and the parasympathetic nervous system (PSNS). Such sites include autonomic nerves (including pre- and post-ganglionic fibers of the ANS), autonomic ganglia, and autonomic plexus. Preferably, the neural target site is a part of the SNS, such as a sympathetic ganglion, a sympathetic nerve or a sympathetic plexus. Regarding sympathetic ganglia, the neural target site can be a prevertebral ganglion or a paravertebral ganglion (sympathetic nerve chain ganglion) or the sympathetic trunk. Examples of paravertebral ganglia include a cervical ganglion, a thoracic ganglion, a lumbar ganglion, and a sacral ganglion. Cervical ganglia include a superior cervical ganglion, a middle cervical ganglion, and an inferior cervical ganglion (or a stellate ganglion). Examples of prevertebral ganglia include a celiac ganglion, an aorticorenal ganglion, a superior mesenteric ganglion, and an inferior mesenteric ganglion. Regarding sympathetic nerves, the neural target site can be a splanchnic nerve, including a greater, lesser, and least splanchnic nerve. Regarding autonomic plexus, the neural target site can be a superior hypogastric plexus or a pulmonary plexus. Further regarding the PNS, the neural target site can be a spinal nerve, a spinal ganglion, a spinal plexus or a localized intrinsic nervous system of an organ. For example, the neural target site can be a dorsal root ganglion, a lumbar plexus, or a hypogastric nerve.

In certain embodiments, the neural target site is preganglionic fibers in the spinal cord efferent fibers and the intermediolateral column; epidural spinal cord; ventral (VRG) and dorsal roots (DRG); DRG afferent fibers, the doral horn; white rami; gray rami; sympathetic ganglia and the sympathetic chain, thoracic splanchnic nerves; para-aortic ganglia, such as the celiac ganglion; sympathetic plexus; or post-ganglionic fibers.

The neural target site can also be an excitatory or inhibitory interneuron. Chemogenetic silencing of excitatory interneurons can be sufficient to reverse aberrant sympathetic nervous system hyperexcitability and subsequent immune suppression. Specifying, the therapy delivery device can be programmed to inhibit or activate Vglut2+ interneurons or VGAT+ inhibitory interneurons.

The neural target site for improving an inflammatory disorder can also be a dermatome specific to the lumbar or thoracic levels of the spinal cord and organ specific head zones. The neural target site can also be nerves that innervate or receive input from the endocrine, lymphatic or pulmonary systems, including the spleen, bone marrow, immune cells, adrenal gland and lungs. Furthermore, the neural target site can be a cutaneous nerve.

In preferred embodiments, a neural target site for improving an inflammatory disorder is the thoracic or lumbar spinal cord and all accessible nerve roots including efferent and afferent nerve roots. In a further preferred embodiment, the neural target site is a T-1 to L-5 spinal cord segment or a T-1 to L-5 nerve root. In other embodiments, the target site is at the level of T5-T9 spinal segments, for example, when modulating systemic immune function. In other preferred embodiments, the neural target site is a greater, lesser and least splanchnic nerve; an afferent nerve receiving input from tissues and organs of the endocrine, lymphatic or pulmonary system; an efferent nerve innervating tissues and organs of the endocrine, lymphatic or pulmonary systems; a dorsal root ganglion; a pre- or post-ganglionic autonomic nerve; a celiac ganglion; a pulmonary plexus; a superior mesenteric ganglion; an aorticorenal ganglion; an inferior mesenteric ganglion; a superior hypogastric ganglion; or a lumbar plexus.

In any of the methods described herein and as described in more detail below, pharmacotherapy can be used as adjuvant therapy together with neuromodulation. Pharmacotherapy can include medications that shift the patient's autonomic tone such as, for example, beta blockers, angiotensin converting enzyme (ACE) blockers, clonidine, anti-spasticity, and anti-convulsive drugs. Pharmacotherapies can also include medications or combinations of medications that can mimic or replace the effects of neuromodulation on the immune system. Such drugs can be used alone or in combination with neuromodulation. Such drugs include, for example, select adrenergic receptor blockers that target alpha or beta (e.g., B1, B2 and B3) adrenergic receptors found on immune cells or glucocorticoid receptor antagonists. Other agents include ganglion blockers such as mecamylamine and alcohol instillations. Pharmacotherapy can include, for example, biologics (such as genetically-engineered proteins derived from human genes). Medications can also include anti-inflammatory agents (such as, for example, steroids and NSAIDs). Pharmacotherapies can also include medications or combinations of medications that can mimic or replace the effects of neuromodulation on the immune system. Such drugs can be used alone or in combination with neuromodulation. Such drugs include, for example, select adrenergic receptor blockers that target alpha or beta (e.g., B1, B2 and B3) adrenergic receptors found on immune cells or glucocorticoid receptor antagonists. Other agents include ganglion blockers such as mecamylamine and alcohol instillations. The medications can be incorporated with polymers to slowly release analgesic, anti-inflammatory, or immune modulators, for example. The medications can also take the form of slow release injectable pellets or chips that modulate the sympathetic nervous system for 3-6 months or another duration of time. Such pellets or chips can be delivered via percutaneous injection and can be used instead of a long-term mechanical neurostimulator. Biologics that can be used include, for example, Abatacept, Adalimumab, Anakinra, Certolizumab pegol, Etanercept, Etanercept-szzs, Golimumab, Infliximab, Rituximab Tocilizumab or Tofacitinib.

Figure 2:
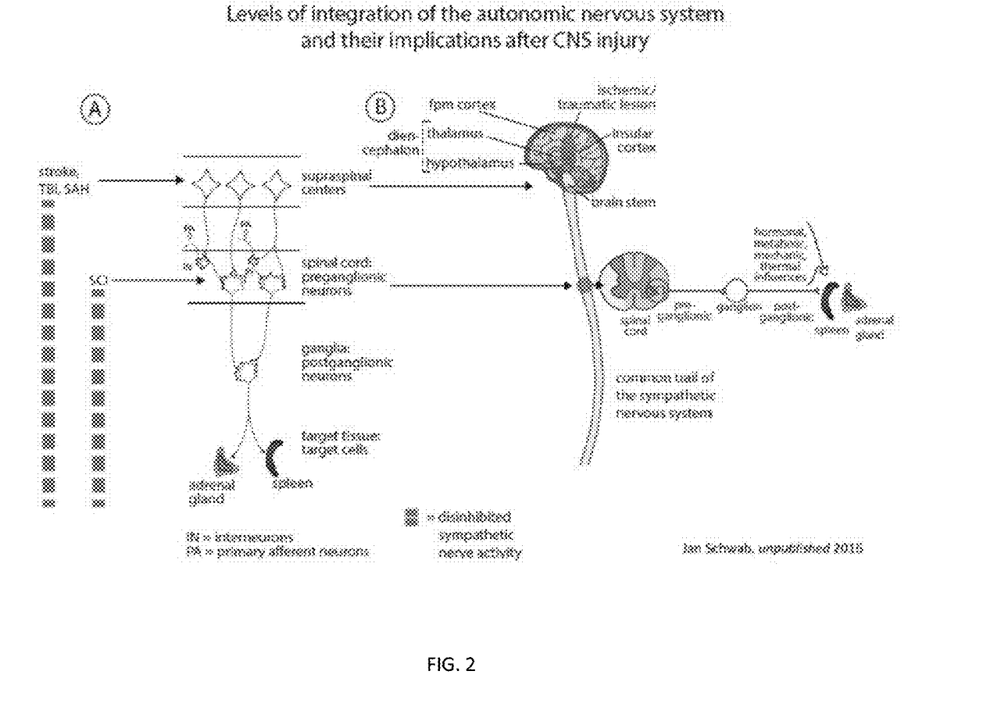

In certain embodiments, a method of improving an inflammatory disorder in a subject involves positioning a therapy delivery device on a neural target site of a maladaptive sympathetic reflex or disturbance of the subject. A maladaptive sympathetic reflex or disturbance is imbalanced sympathetic nerve activity that enters the lymphatic organs (e.g., spleen, bone marrow); endocrine organs such as the liver or adrenal gland; or immune system organ or immune systems cells as illustrated in FIG. 2. A maladaptive sympathetic reflex or disturbance causes abnormal immune activity such as decreased, increased, imbalanced, or impaired immune activity as compared to the immune activity of a healthy subject. A healthy subject is a subject who has not previously been diagnosed as having any signs or symptoms indicating the presence of immune system dysfunction, a history of immune system dysfunction, or evidence of immune system dysfunction. A healthy subject is also a subject who, if examined by a medical professional, would be characterized as free of immune system dysfunction.

A maladaptive sympathetic reflex or disturbance can be disinhibited sympathetic nerve activity that enters the lymphatic organs or immune system organs. A maladaptive reflex or disturbance includes a sympathetic anti-inflammatory reflex, Sympathico-Babinski, disinhibited spinally generated sympathetic activity, and paroxysmal sympathetic activity. These conditions generally act on the ANS causing a systemic immune-suppression or immune-activation. A maladaptive sympathetic reflex or disturbance can be present in a subject with a hyperactive or hypoactive immune system. Further, a maladaptive sympathetic reflex or disturbance can be present after CNS injury including injury to the brain, such as stroke, TBI, and subarachnoid heamorrhage (SAH); SCI; and other CNS or spinal cord or nervous system damage/injury, such as damage to nerves. Injury can be due to acute or chronic degenerative conditions. Chronic degeneration conditions include injury to the brain or spinal cord by compressive tumor growth but also degenerative myelopathy and neurodegenerative disease.

Figure 4:
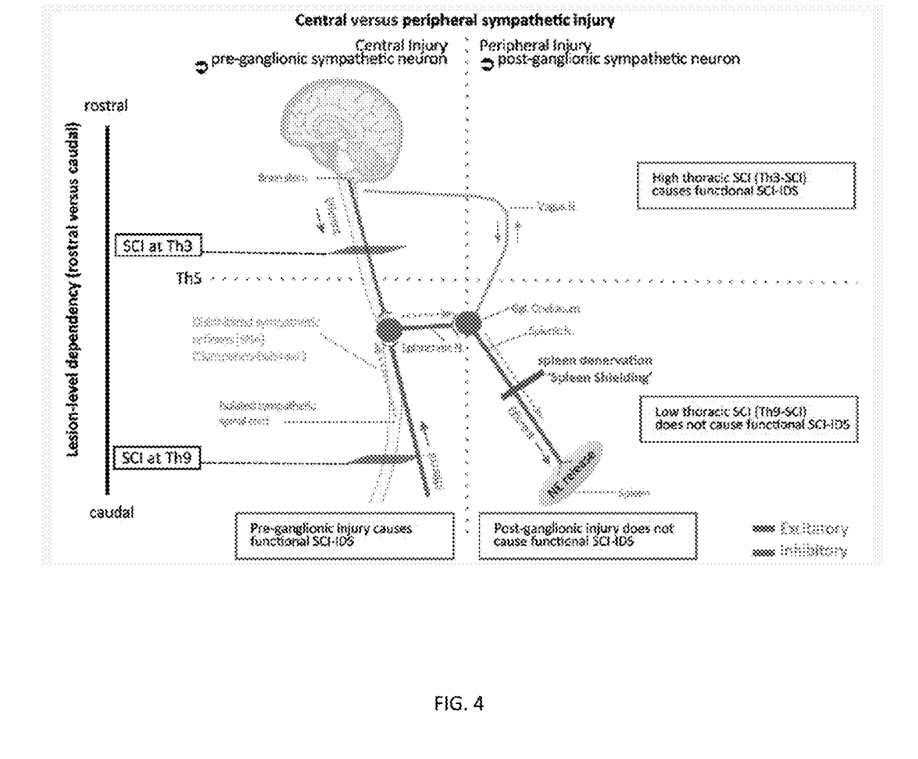
FIG. 4 is a schematic illustration of the neurogenic pathophysiology and targets of maladaptive sympathetic signaling perpetuating functional spinal cord injury induced immune depression syndrome after spinal cord injury.

Without wishing to be bound by theory, FIG. 4 schematically illustrates the neurogenic pathophysiology and targets of maladaptive sympathetic signaling perpetuating functional SCI-IDS after SCI. Under physiological conditions, excitatory sympathetic signals are controlled by supraspinal inhibition. After SCI, loss of supraspinal control leads to spinally generated SNA. SNA originates below SCI injury and leads to maladaptive efferent sympathetic activity signaling to the spleen, via the splenic or splanchnic nerve and directly to the adrenal gland. Such activity can culminate in large excitatory spinal sympathetic reflexes. Spinal sympathetic reflexes occur in analogy to pathological Babinski motor reflexes, which are caused by a loss of supraspinal (bulbospinal) tonic inhibition ("Sympathetic-Babinski"). Again, without wishing to be bound by theory, disinhibited spinal generated SNA after high thoracic (Th3) SCI can lead to ad hoc induction of excitatory SNA burst entering the splenic nerve and adrenal gland associated with increased levels of norepinephrine (NE) in the circulation and the spleen, which in turn causes apoptosis of immune cells in the spleen and other lymphoid organs. This results in a decrease of spleen size, partial loss of immune cells and an elevated susceptibility to infection. Blocking SNA signaling ("shielding") by preceding peripheral denervation of the splenic nerve ameliorates functional SCI-IDS and bacterial load after Th3-SCI. Moreover, the peripheral splenic nerve can be a target for immunomodulation after SCI in order to restore impaired host defense after SCI (SCI-IDS) by blocking SNA to the spleen. As such, spleen and adrenal gland shielding can be an interventional strategy to ameliorate functional SCI-IDS to prevent infections in patients at risk.

Again, without wishing to be bound by theory, it is believed that enhancing the maladaptive sympathetic reflex or disturbance may also artificially immune-suppress a patient and may attenuate immune diseases, including inflammatory disorders affecting all systems of the body. Those systems include, but are not limited to, the nervous system (peripheral and central), bone, cartilage, bronchial system/lung, pancreas, liver, and hematological systems. Blocking sympathetic activation reactive to stress responses may harness a patient's immune defense system against cancer. Other conditions causing immune suppression and elevated risk for infections are listed in Table I below.

Table I

| Term |
|---|
| Epileptogenic |
| tonic decerebrate seizures |
| autonomic seizures with decerebrate seizures |
| diencephalic (autonomic) seizures/epilepsy/fits |
| autonomic sympathetic seizures |

-continued

| Term |
|---|
| Structural |
| brain stem attack |
| hypothalamic-midbrain dysregulation syndrome |
| acute midbrain syndrome |
| acute hypothalamic instability |
| hypothalamic storm |
| Clinically Descriptive |
| paroxysmal hypertension associated with disphoresis |
| (central) autonomic dysfunction/syndrome |
| hyperthermic syndrome |
| neuroleptic malignant-like syndrome |
| autonomic storms/storming |
| autonomic hyperactivity |
| dysautonomia |
| (central) autonomic instability |
| hyperpyrexia with sustained muscle contraction |
| autonomic dysregulation |
| paroxysmal sympathetic storms |
| sympathetic storms/storming |
| autonomic disorder (and spasticity) |
| neuro storm |
| paroxysmal autonomic instability with dystonia |
| hyperadrenergic state |
| paroxysmal autonomic instability |
| dysautonomic crises |
| arc de cercle and dysautonomia |
| storming: transient autonomic dysfunction |
| paroxysmal sympathetic hyperactivity |
| hypermetabolic paroxysmal dysautonomia |

Accordingly, in certain embodiments, the therapy signal blocks neural conduction in the neural target site. Such blocking of neural conduction can reduce or balance the patient's sympathetic tone to improve the patient's immune response. In certain embodiments, the patient is suffering from sepsis, a central nervous system injury, antibiotic resistance, compensatory anti-inflammatory response syndrome (CARS), chronic inflammatory response syndrome (CIRS), CNS injury-induced immune deficiency syndrome (CIDS), including stroke-induced immune deficiency syndrome (SIDS), SCI-IDS, traumatic brain injury-induced immune depression syndrome (TBI-IDS), or other immune deficiencies.

In certain embodiments, the therapy signal stimulates neural conduction in the neural target site. Such stimulation can enhance the patient's sympathetic tone to immune-suppress the patient, suppress the patient's baseline sympathetic tone to suppress disease-associated increases in immune function, or increase activity of the patient's intact sympathetic circuitry to suppress the patient's immune function. Such stimulation can be used in circumstances where the patient has undergone organ transplantation (including bone marrow transplantation); suffers from an autoimmune disorder, including multiple sclerosis, rheumatoid arthritis, myasthenia gravis or myositis; suffers from corticosteroid side effects including osteoporosis or cortisone-induced psychosis; or suffers from other adverse effects from immune suppressive therapies.

Other conditions include hyper-immune disorders including multiple sclerosis, rheumatoid arthritis, and allergic conditions. Conditions also include hypo-active immune system disorders such as cancers or infections.

Figure 3:
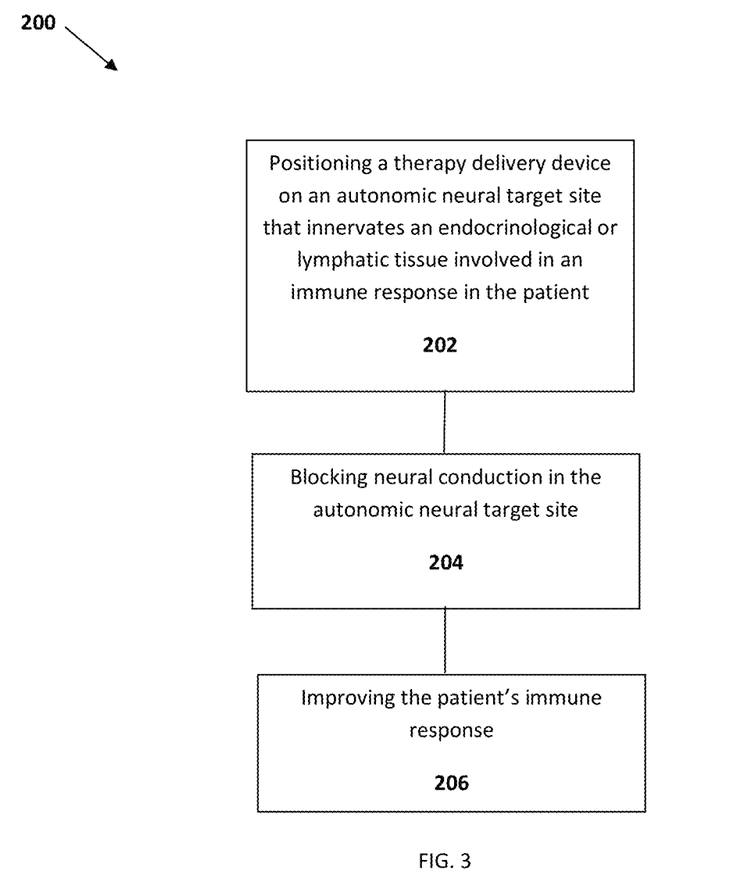
FIG. 3 is a process flow diagram illustrating a method for improving an immune response in a patient according to an embodiment of the present disclosure.

Referring to FIG. 3, in other embodiments, the present disclosure provides a method of improving an immune response in a patient suffering from a condition resulting or caused by an abnormal or deficient immune system 200. The method includes positioning a therapy delivery device on an autonomic neural target site that innervates an endocrinological or lymphatic tissue involved in an immune response in the patient 202. The method further includes blocking neural conduction in the autonomic neural target site 204 and improving the patient's immune response 206. The autonomic neural target site can be a celiac ganglion, a superior mesenteric ganglion, an aorticorenal ganglion, a renal plexus, a inferior mesenteric ganglion, a superior hypogastric ganglion or a lumbar plexus. The condition can be, for example, sepsis, a central nervous system injury, antibiotic resistance, CARS, CIRS, SCI-IDS, TBI-IDS, or CIDS.

In certain aspects, the present disclosure includes various therapy delivery devices (not shown) and related systems configured to modulate a patient's immune response to improve an inflammatory disorder in the patient. In some instances, therapy delivery devices may be positioned directly on a target nerve, neuron or nerve structure. For example, with respect to the enteric nervous system, the therapy delivery device may be directly implanted in the submucosal (Meissner's) or myenteric (Auerbach's) plexus of the GI mucosa or muscularis propria, respectively. In other instances, therapy delivery devices may be positioned below the skin of a mammal but not directly on a target nerve, neuron or nerve structure. In further instances, therapy delivery devices may comprise an external device, e.g., positioned in a lumen adjacent a target nerve, neuron or nerve structure. In still further instances, therapy delivery devices can include an external device, e.g., positioned on the skin of a mammal adjacent a target nerve, neuron or nerve structure. Therapy delivery devices can be temporarily or permanently implanted within, on, or otherwise associated with a subject in need of immune function modulation.

Therapy delivery devices can be configured or programmed to deliver various types of therapy signals to a target nerve, neuron or nerve structure. For example, therapy delivery devices can be configured or programmed to deliver only electrical energy, only a pharmacological or biological agent, or a combination thereof. In one example, therapy delivery devices can comprise at least one electrode and an integral or remote electrical energy generator (not shown), which is in electrical communication with the one or more electrodes and configured to produce one or more electrical signals (or pulses). In another example, therapy delivery devices can include a pharmacological or biological agent reservoir, a pump, a fluid dispensing mechanism, or a long-lasting polymer that encapsulates the drug in the form of a pellet, sheet or other form, for example, to allow slow infusion or delivery of medications and other agents that can modulate nervous system activity. Non-limiting examples of pharmacological and biological agents include chemical compounds, drugs, nucleic acids, polypeptides, stem cells.

The therapy delivery device can also be configured or programmed to deliver various other energy forms within the energy spectrum and/or biological forms of therapy, such as, for example, sound waves, ultrasound, radiofrequency (continuous or pulsed), optical, infrared, microwave, magnetic waves, cryotherapy, heat, or optogenetic therapy.

In yet another example, therapy delivery devices can be configured or programmed to deliver magnetic nerve stimulation with desired field focality and depth of penetration. Combinations of the therapy delivery devices above are also included within the scope of the present disclosure.

In some instances, therapy delivery devices can include a stimulator (or inhibitor), such as an electrode or electrical lead, a controller or programmer, and one or more connectors for connecting the stimulating (or inhibiting) device to the controller. In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode can be controllable to provide output signals that may be varied in voltage, frequency, pulse-width, current and intensity. The electrode can also provide both positive and negative current flow from the electrode and/or is capable of stopping current flow from the electrode and/or changing the direction of current flow from the electrode. In some instances, therapy delivery devices can include an electrode that is controllable, i.e., in regards to producing positive and negative current flow from the electrode, stopping current flow from the electrode, changing direction of current flow from the electrode, and the like. In other instances, the electrode has the capacity for variable output, linear output and short pulse-width. In other instances, the electrode can comprise a coil configured to deliver magnetic stimulation.

The electrical energy generator can comprise a battery or generator, such as a pulse generator that is operatively connected to the electrode. For example, the electrical energy generator can include a battery that is rechargeable by inductive coupling. The electrical energy generator may be positioned in any suitable location, such as adjacent the electrode (e.g., implanted adjacent the electrode), or a remote site in or on the mammal's body or away from the mammal's body in a remote location. An electrode may be connected to the remotely positioned electrical energy generator using wires, e.g., which may be implanted at a site remote from the electrode or positioned outside the mammal's body. In one example, implantable electrical energy generators analogous to a cardiac pacemaker may be used.

Internal power sources can obtain sufficient energy, for example, from muscle movements, aortic pulsations, peristalsis, and other source of body energy generation that can be harnessed via a capacitor or a balloon device that harnesses the energy, for example, so that an internal battery, IPG, or external power source is not needed.

An electrical signal may be constant, intermittent, varying and/or modulated with respect to the current, voltage, pulse-width, waveform, cycle, frequency, amplitude, and so forth. For example, a current may range from about 0.001 to about 1000 milliampere (mA) and, more specifically, from about 0.1 to about 100 mA. Similarly, the voltage may range from about 0.1 millivolt to about 25 volts. The frequency may range from about 0.5 to about 20,000 Hz. The pulse-width may range from about 10 to about 10,000 microseconds. The waveform can be a sine wave, a square wave, or the like. The type of stimulation may vary and involve different waveforms. For example, the stimulation may be based on the H waveform found in nerve signals (i.e., Hoffinan Reflex). In another example, different forms of interferential stimulation may be used.

To increase activity in a portion of the neural target site such as the ANS, for example, voltage or intensity may range from about 0.1 millivolt to about 1 volt or more, e.g., 0.1 volt to about 50 volts (e.g., from about 0.2 volt to about 20 volts), and the frequency may range from about 1 Hz to about 100 Hz (e.g., from about 2 Hz to about 100 Hz). In some instances, pure DC voltages may be employed and in other instance AC may be employed. The pulse-width may range from about 1 microsecond to about 2000 microseconds or more, e.g., from about 10 microseconds to about 1000 microseconds (e.g., from about 10 microseconds to about 1000 microseconds). The electrical signal may be applied for at least about 1 millisecond or more, e.g., about 1 second (e.g., about several seconds). In some instances, stimulation may be applied for as long as about 1 minute or more, e.g., about several minutes or more (e.g., about 30 minutes or more).

To decrease activity in a portion of the neural target site including the ANS, for example, voltage or intensity may range from about 1 millivolt to about 1 volt or more, e.g., 0.1 volt to about 50 volts (e.g., from about 0.2 volt to about 20 volts), and the frequency may range from about 1 Hz to 100 Hz or from 100 Hz to ultrahigh frequency of 10,000 or 20,000 Hz. In some instances, pure DC voltages may be employed. The pulse-width may range from about 1 microseconds to about 2000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, the electrical energy may be applied for as long as about 1 minute or more, e.g., about several minutes or more (e.g., about 30 minutes or more may be used). The stimulation may be continuous or of intermittent durations of as little a 1 minute to as long as 24 hours.

The electrode may be mono-polar, bipolar or multi-polar of any configuration and geometry to fit the desired target of interest. Further, the electrode (and any wires and optional housing materials) can be made of inert materials, such as silicon, metal, plastic and the like. In one example, a therapy delivery device can include a multi-polar electrode having about four exposed contacts (e.g., cylindrical contacts).

A controller or programmer may also be associated with a therapy delivery device. A programmer, for example, can include one or more microprocessors under the control of a suitable software program. The programmer can include other components such as an analog-to-digital converter, etc.

Therapy delivery devices can be pre-programmed with desired stimulation parameters. Stimulation parameters can be controllable so that an electrical signal may be remotely modulated to desired settings without removal of the electrode from its target position. Remote control may be performed, e.g., using conventional telemetry with an implanted electric signal generator and battery, an implanted radiofrequency receiver coupled to an external transmitter, and the like. In some instances, some or all parameters of the electrode may be controllable by the subject, e.g., without supervision by a physician. In other instances, some or all parameters of the electrode may be automatically controllable by a programmer or controller comprising the therapy delivery device.

The therapy delivery device can be configured for different forms of placement, insertion or implantation. This includes, for example, direct stimulation, epidural stimulation, and indirect stimulation, external or internal stimulation, or transluminal stimulation. Neural target sites can be approached via direct open surgical procedures; or indirect procedures such as percutaneous, subcutaneous, transcutaneous, transvascular (including transvenous), transesophageal, transabdominal, or other forms of indirectly modulating the neural target site. The neural target site can also be accessed via an endoscopic procedure.

In one example, the therapy delivery device can be configured for percutaneous placement or implantation. In this instance, the therapy delivery device can comprise one or more implantable electrodes shaped or configured, for example, as a wire, a rod, a filament, a ribbon, a cord, a tube, a formed wire, a flat strip, pellet, or a combination thereof. In one example, one or more of the electrodes can comprise a laminotomy electrode array. Laminotomy electrodes, for example, generally have a flat paddle configuration and typically possess a plurality of electrodes (e.g., 2, 3, 4 or more) arranged on the paddle. The arrangement of electrodes on the paddle may be in rows and columns, staggered, spaced, circular, or any other arrangement that will position the electrodes for optimal delivery of electrical energy. The one or more implantable electrodes may be controlled individually, in series, in parallel, or any other manner desired. Once implanted, the implantable electrode(s) may be held in position using various fixation devices, such as stitches, epoxy, tape, glue, sutures, or a combination thereof.

In another example, the device can be configured for transvascular placement or implantation. For example, the therapy delivery device can be placed across the azygous vein, vena cava or another venous and arterial system adjacent to the structure innervating or influencing the patient's immune function.

In another example, the therapy delivery device can be configured for intravascular or intraluminal placement or implantation using passive leads that anchor to the wall of the vessel for example. In some instances, a therapy delivery device configured for intravascular or intraluminal placement or implantation can be configured in an identical or similar manner as the expandable electrode disclosed in U.S. patent application Ser. No. 11/641,331 to Greenberg et al. (hereinafter, "the '331 application"), which is incorporated by reference herein. In some instances, the therapy delivery device is a passive lead with wire anchors that attach to the vessel wall via a zigzag pattern that is separate from an electrically active stent.

In yet another example, the therapy delivery device can be configured for transcutaneous neuromodulation. In some instances, transcutaneous neuromodulation can include positioning an electrode on a skin surface so that a therapy signal can be delivered to a target nerve, neuron, or nerve structure. In other instances, transcutaneous neuromodulation can include positioning an electrode, without penetrating the skin of the subject and without necessarily contacting the electrode with the skin surface, so that a therapy signal can be delivered to a target nerve, neuron, or nerve structure. Transcutaneous neuromodulation can additionally include partially transcutaneous methods (e.g., using a fine, needle-like electrode to pierce the epidermis). In another example, a surface electrode can be placed into electrical contact with a nerve, neuron, or nerve structure (e.g., of the ANS) associated with immune function. Generally, an electrical signal used for transcutaneous neuromodulation may be constant, varying and/or modulated with respect to the current, voltage, pulse-width, cycle, frequency, amplitude, and so forth (e.g., the current may be between about 0.1 to 100 milliamps), about 1-30 V (average), about 1 to about 10,000 Hz, with a pulse-width of about 10 to about 5000 microseconds.

Devices for transcutaneous neuromodulation can have a variety of configurations. In some instances, a transcutaneous therapy delivery device may be configured as a belt or strap having at least one electrode operably attached thereto. A therapy delivery device can be incorporated into clothing (such as, for example, a neck collar, brace, sweater, shirt, pants, socks, glove, stocking, skirt, shoes, underwear, vest, necklace, scarf, wrist band, waist band, ring, other jewelry, sportswear, ear pieces, adhesive patches, stickers, skin tattoos, skin paint, or a neuro-paint of other inductive and coupling material). In addition, a therapy delivery device can be embedded in a pillow, a bed, a head rest of a chair, a car seat, a car neck rest, a computer console, and other types of furniture. These devices can provide either electrodes for delivering a therapy signal, sensors, or a combination of both.

Therapy delivery devices can be part of an open- or closed-loop system. In an open-loop system, for example, a physician or subject may, at any time, manually or by the use of pumps, motorized elements, etc., adjust treatment parameters, such as pulse amplitude, pulse-width, pulse frequency, duty cycle, dosage amount, type of pharmacological or biological agent, etc. Alternatively, in a closed-loop system, treatment parameters (e.g., electrical signals) may be automatically adjusted in response to a sensed physiological parameter or a related symptom indicative of the extent of immune function. In a closed-loop feedback system, a sensor that senses a physiological parameter associated with immune function can be utilized. More detailed descriptions of sensors that may be employed in a closed-loop system, as well as other examples of sensors and feedback control techniques that may be employed as part of the present disclosure are disclosed in U.S. Pat. No. 5,716,377, which is incorporated by reference herein.

It should be appreciated that incorporating the therapy delivery device as part of a closed-loop system can include placing or implanting a therapy delivery device on or within a mammal at a nerve target site, sensing a physiological parameter associated with immune function, and then activating the therapy delivery device to apply a therapy signal to adjust application of the therapy signal to the nerve target site in response to the sensor signal to modulate immune function. In certain instances, the physiological parameter is associated with a deficient or abnormal immune system such as a hypoactive or hyperactive immune system. In some instances, such physiological parameters can include any characteristic or function associated with immune function, such skin temperature, protein concentrations, heart rate, blood pressure, biomarkers of the immune system or autonomic nervous system, electrochemical gradients, electrolytes, laboratory values, body temperature, and vital signs.

Sensors to measure physiological parameters can be external of the patient's body, or on the patient's body. The parameters can be measured, for example, from blood, saliva, or sweat biomarkers. Non-limiting examples of physiological parameters include vital signs; EEG, EMG; FNIRS; heart rate variability; immune and hormonal markers, IL-6, TNF, other inflammatory mediators; sedimentation rate such as ESR for example, CRP, CBC and differential ratios of cell; circadian rhythms; and other means of feedback linked to stimulation modulation. Physiological parameters that are biomarkers include but are not limited to BDNF, Neuropeptide Y, cortisol, orexin, oxytocin, epinepherine, melatonin norepinephrine, DHEA, IL-6, IL-1, IL-4, TNF. Other physiological parameters include eye tracking, pupil tracking, facial expression, thermography, and cognitive and behavioral measures such as stress, anxiety or hyperactivity.

The GI tract and enteric nervous system (ENS) may be locations where a closed-loop system could be employed to improve GI inflammation. For example, if a therapy delivery signal is delivered to the spinal cord, a prevertebral ganglion or vagus nerve, a receiving electrode or a biosensor (e.g., a biomaterial coated with detection surfaces for specific neurotransmitters) can be implanted into an enteric plexus or ganglion. When sufficiently activated, the biosensor can be programmed to shut off the efferent/afferent signal.

Figure 5:
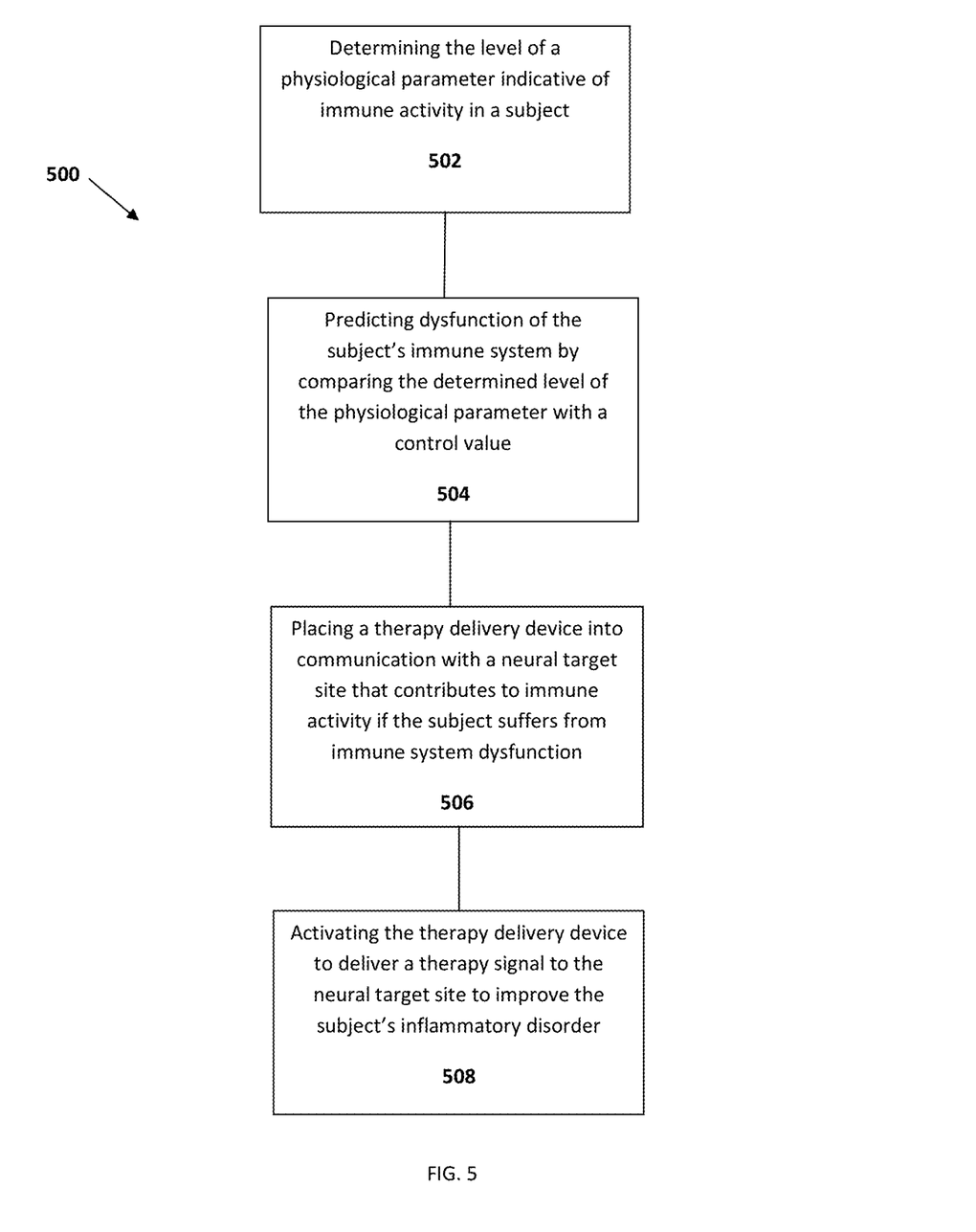
FIG. 5 is a process flow diagram illustrating a method for improving an inflammatory disorder in a subject according to an embodiment of the present disclosure.

With reference to FIG. 5, the present disclosure provides another method 500 for improving an inflammatory disorder in a subject. Such a method comprises determining the level of a physiological parameter that is indicative of immune activity 502 of the subject and predicting dysfunction of the subject's immune system by comparing the determined level of the physiological parameter with a control value 504. The method further includes placing a therapy delivery device into communication with a neural target site that contributes to immune activity if the subject suffers from immune system dysfunction 506. The method further includes activating the therapy delivery device to deliver a therapy signal to the neural target site to improve the subject's inflammatory disorder 508.

With respect to determining a level of a physiological parameter indicative of immune activity, non-limiting physiological parameters include: leukocyte subset ratios, such as the CD4/CD8 ratio; immunoglobulin (antibody) levels or antigen-specific antibody levels (e.g., antibodies directed against specific proteins in the body); NK lysis; granulocyte, neutrophil or monocytic activation; levels of biomarkers of inflammation such as, for example, C-reactive protein; levels of biomarkers of infection such as, for example, procalcitonin; or levels of lymphocytes or leukocytes. The above-described physiological parameters are exemplary. Other physiological parameters can be detected depending on various factors. Such factors include, for example, the specific inflammatory disorder being treated, the subject's age, the body organs affected, the duration or phase of the disorder, and other factors.

Various assays, tests and procedures can be employed to determine the level of a physiological parameter indicative of immune activity. For example, flow cytometry analysis can be used to determine the ratio of leukocyte subsets, such as the CD4/CD8 ratio; blood analysis can be used to determine antibody levels or antigen-specific antibody levels; immune cell function assays (e.g., mitogen stimulation of lymphocytes with cytokine readouts or proliferation; NK cell lysis assays; or radiological testing, such as T1/T2-weighted imaging of the brain or spinal cord with gadolinium chloride enhancement to identify regions of vascular compromise which are either caused by aberrant inflammation or cause it to develop. The above-described assays, tests and procedures are exemplary. Other techniques can be used to determine the level of a physiological parameter indicative of immune activity depending on various factors. Such factors include, for example, the specific inflammatory disorder being treated, the subject's age, the body organs affected, the duration or phase of the disorder, and other factors.

After determining the level of the physiological parameter, the detected level can be compared to a control value to determine if the detected level is abnormal, thereby indicating that the subject suffers from an immune system dysfunction. Control values can be based upon the level of a corresponding physiological parameter obtained from a control population. The control population can be the general population or a select population. The select population can be a group of healthy subjects, a group of subjects that are at risk of immune system dysfunction, or a group of subjects that suffer from immune system dysfunction. For example, if the level of the physiological parameter is the units of a particular biomarker per ml of blood, the control value can be based upon the units of the particular biomarker per ml of blood in subjects of the general or select population.

As stated above, after comparing the detected level of the physiological parameter with the control value, a determination can be made as to whether the subject has immune system dysfunction. In some instances, an increased level of the detected physiological parameter (as compared to the control value) can be indicated of immune system dysfunction. In other instances, a decreased level of the detected physiological parameter (as compared to the control value) can be indicative of immune system dysfunction. For example, CD4/CD8 ratios are often used as indicators of "adaptive immune health" with a normal ratio of greater than 2.0. Values lower than 2.0 are often used clinically as a diagnostic criteria for various suspected immune diseases including HIV, AIDS, anemia, multiple sclerosis, and chronic infections. A ratio higher 2.0 could indicate the presence of an infection. Furthermore, prolonged elevation of inflammatory markers, such as a C-reactive protein level greater than 5 mg/l, is often associated with exacerbated inflammatory disease; prolonged elevation of markers of infection, such as a procalcitonin level greater than 0.5 ng/ml or a leukocyte level greater than 9 nl, is often associated with exacerbated infectious disease; prolonged suppression of lymphocytes, such as a lymphocyte level less than 1.5/nl or a leukocyte level of less than 4/nl, is often associated with exacerbated immune-suppression or impaired host defense. Other indicators of immune system dysfunction include the presence of pathogenic antibodies; excessive NK lysis; the presence of innate cell respiratory burst function such as granulocyte, neutrophil and monocytic activation; enhanced lesions indicating a break-down of the blood-brain barrier; or the presence of sustained leucopenia, leukocytosis, lymphopenia, lymphocytosis, monocytosis, monopenia, neutrophilia, or neutropenia. The above-described factors and values are exemplary and other factors and values can indicate whether a subject has immune system dysfunction.

The foregoing description and examples have been set forth merely to illustrate the invention and are not intended as being limiting. Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance. Further, an additional step of methods of the present disclosure includes identify a patient suffering from an inflammatory disorder. Furthermore, all references cited herein are incorporated by reference in their entirety.

The following is claimed:

1. A method of improving an inflammatory disorder in a subject suffering therefrom comprising:
   positioning a therapy delivery device in communication with a neural target site, comprising at least a part of the enteric nervous system, that contributes to immune activity of the subject;
   sensing, by at least one of an electrical sensor and a biological sensor, at least one physiological parameter of immune activity of the enteric nervous system that is indicative of an inflammatory disorder of the subject, wherein the at least one of the electrical sensor and biological sensor is disposed at an enteric plexus or ganglion;
   delivering, by the therapy delivery device, a therapy signal to the neural target site, wherein delivery parameters of the therapy signal are selected based on the sensed at least one physiological parameter to modulate an immune response of the subject to treat the subject's inflammatory disorder.

2. The method of claim 1, wherein inflammatory disorder comprises atherosclerosis.

3. The method of claim 1, wherein the inflammatory disorder comprises myocarditis, nephritis, prostatitis, sinusitis, or organ-based inflammation.

4. The method of claim 1, wherein the inflammatory disorder comprises joint inflammation.

5. The method of claim 1, wherein the inflammatory disorder comprises non-allergic asthma.

6. The method of claim 1, wherein the inflammatory disorder comprises an inflammatory bowel disease.

7. The method of claim 6, wherein the inflammatory bowel disease is Crohn's disease or ulcerative colitis.

8. The method of claim 1, wherein the inflammatory disorder comprises acute respiratory distress syndrome (ARDS) or chronic respiratory distress syndrome (CRDS).

9. The method of claim 1, wherein the inflammatory disorder comprises acute lung injury.

10. The method of claim 1, wherein the inflammatory disorder comprises neurogenic lung edema.

11. The method of claim 1, wherein the subject is livestock.

12. The method of claim 1, wherein the subject is a human.

13. The method of claim 1, wherein the neural target site comprises a thoracic or lumbar segment of the spinal cord.

14. The method of claim 13, wherein the thoracic segment is a T5-T-9 thoracic segment.

15. The method of claim 1, wherein the neural target site comprises a thoracic or lumbar spinal nerve root.

16. The method of claim 1, wherein the neural target site comprises a neural target site selected from the group consisting of a celiac ganglion, an aorticorenal ganglion, a pulmonary plexus, a superior mesenteric ganglion, an inferior mesenteric ganglion, a superior hypogastric ganglion, a lumbar plexus, a sympathetic chain ganglion, a greater splanchnic nerve, a lesser splanchnic nerve, a least splanchnic nerve, and a dorsal root ganglion.

17. The method of claim 1, wherein the neural target site comprises a dermatome specific to thoracic or lumbar levels of a spinal cord of the subject.

18. The method of claim 1, wherein the neural target site comprises a nerve that innervates or receives input from the spleen, bone marrow, the thymus, a lymph node, immune cells, the kidney, the adrenal gland or the lungs.

19. A method of improving an inflammatory disorder in a subject comprising:
   sensing, by at least one of an electrical sensor and biological sensor, the level of at least one physiological parameter that is indicative of immune activity of the enteric nervous system of the subject, wherein the at least one of the electrical sensor and biological sensor is disposed at an enteric plexus or ganglion;
   predicting dysfunction of the subject's immune system by comparing the determined level of the at least one physiological parameter with a control value and determining, based on the comparison, that the level of the at least one physiological parameter is indicative of an inflammatory disorder of the subject;
   placing a therapy delivery device into communication with a neural target site, comprising at least a part of the enteric nervous system, that contributes to immune activity of the subject; and delivering, by the therapy delivery device, a therapy signal to the neural target site, wherein delivery parameters of the therapy signal are selected based on the sensed at least one physiological parameter to modulate an immune response of the subject to treat the subject's inflammatory disorder.

\* \* \* \* \*